(12) United States Patent
Bassuk et al.

(10) Patent No.: US 6,723,086 B2
(45) Date of Patent: Apr. 20, 2004

(54) REMOTE CONTROLLED TRANSDERMAL MEDICATION DELIVERY DEVICE

(75) Inventors: William K. Bassuk, St. Louis, MO (US); Ralph S. Hughes, Chandler, AZ (US); Vince E. Birdwell, Mesa, AZ (US)

(73) Assignee: Logiq Wireless Solutions, Inc., Mesa, AZ (US)

( * ) Notice: Subject to any disclaimer, the term of this patent is extended or adjusted under 35 U.S.C. 154(b) by 398 days.

(21) Appl. No.: 09/850,558

(22) Filed: May 7, 2001

(65) Prior Publication Data

US 2003/0171710 A1 Sep. 11, 2003

(51) Int. Cl.[7] .................. A61K 9/22; A61M 31/00; A61M 37/00; A61M 5/32; A61M 5/00; A61M 35/00

(52) U.S. Cl. ................ 604/890.1; 604/65; 604/140; 604/180; 604/247; 604/289

(58) Field of Search .................... 604/890.1, 891.1, 604/20, 501, 65–67, 99.04, 131, 140, 167.03, 180, 246–249, 257, 289; 607/62

(56) References Cited

U.S. PATENT DOCUMENTS

| | | | | |
|---|---|---|---|---|
| 5,496,273 A | * | 3/1996 | Pastrone et al. | 604/67 |
| 5,860,957 A | * | 1/1999 | Jacobsen et al. | 604/156 |
| 6,096,000 A | * | 8/2000 | Tachibana et al. | 604/20 |
| 6,296,630 B1 | * | 10/2001 | Altman et al. | 604/508 |
| 6,447,474 B1 | * | 9/2002 | Balding | 604/66 |
| 6,454,759 B2 | * | 9/2002 | Krulevitch et al. | 604/891.1 |
| 6,577,899 B2 | * | 6/2003 | Lebel et al. | 607/60 |
| 2002/0040208 A1 | * | 4/2002 | Flaherty et al. | 604/288.01 |
| 2002/0133120 A1 | * | 9/2002 | Yeh | 604/131 |

\* cited by examiner

Primary Examiner—Brian L. Casler
Assistant Examiner—Catherine S. Williams
(74) Attorney, Agent, or Firm—Charlene R. Jacobsen; Lowell W. Gresham; Meschkow & Gresham, PLC

(57) ABSTRACT

A transdermal medication delivery device (20) for the remote controlled administration of medications (68, 70, 72) for absorption through the skin of a patient (22) includes a tubes (62) containing the medications (68, 70, 72). Tubes (62) are in fluid communication with valve inlets (76, 82, 88) of valves (74, 80, 86) formed on a micro-electro-mechanical-system-based (MEMS-based) valve chip (64, 162). A medication delivery component (26, 176) in fluid communication with valve outlets (78, 84, 90) of valves (74, 80, 86) has a surface (66, 178) adapted to be in contact with the skin of the patient (22) when in use. A controller (92) is configured to control a flow of the medications (68, 70, 72) through the valves (74, 80, 86), and a wireless communication interface (94), in communication with the controller (92), is configured to receive a medication control message (96) from a remote location (32). The medication control message (96) instructs the controller (92) to regulate the valves (74, 80, 86) to adjust the flow of the medications (68, 70, 72) from the tubes (62) to the surface (66, 188) of the medication delivery component (26, 176).

18 Claims, 7 Drawing Sheets

REMOTE CONTROLLED TRANSDERMAL MEDICATION DELIVERY DEVICE

TECHNICAL FIELD OF THE INVENTION

The present invention relates to a device for the transdermal delivery of medications. More specifically, the present invention relates to a transdermal medication delivery device capable of remote controlled administration of medication.

BACKGROUND OF THE INVENTION

Individuals with chronic or terminal medical conditions are frequently required to take many different medications on irregular schedules. Often these individuals are hospitalized in order to control the administration of the medications and for monitoring purposes. The hospitalization and discomfort of around-the-clock injections, intravenous medication administration, oral and nasal medication administration, and so forth undesirably lower the quality of life for patients who are suffering from chronic or terminal illnesses. In addition, hospitalization undesirably increases the per patient cost of medical care.

Even, for those ambulatory individuals who are not hospitalized but require long-term medications, the administration of these medications is disadvantageous for the patient. For example, these patients are typically obliged to carry their medications with them at all times, to administer medications at inconvenient times and in awkward locations, or to stay home to follow their medication regime thus decreasing the quality of life for these "ambulatory" patients.

Furthermore, the routes taken to administer these medications have several disadvantages. For example, oral administration is often associated with variable absorption, with blood medication levels sometimes rising to toxic levels or falling to subtherapeutic levels. In addition, oral administration can cause side effects, such as gastrointestinal upset. Injections, whether intramuscular, intravenous, or subcutaneous can be painful, cause scarring, or require extensive training of the patient or caregiver to administer the injections.

The disadvantages associated with these medication schedules and medication routes decrease patient compliance, sometimes causing patients to intentionally omit their treatments. When a patient has several medications, the sheer number of medications and the complexity of the medication administration schedule can also cause treatments to be inadvertently missed or doubled. Yet another problem arises with patients who have impaired mental faculties, such as with some older patients and those suffering from Alzheimer's disease. Patients with impaired mental faculties may simply forget to take their medications.

To overcome some of the problems associated with these medication delivery routes, researchers are increasingly studying the efficacy of administering medications through transdermal delivery, i.e., the absorption of the medications through the skin. Some of the aims of transdermal medication delivery are to maximize the bioavailability of the medication, to optimize the therapeutic value, to minimize side effects, to simplify the administration of the medications, and to generally allow the patient a higher quality of life.

One of the most important advantages of the transdermal medication delivery route is that it provides constant and continuous absorption of the drug, thus keeping blood levels within the "therapeutic window". In addition, through transdermal delivery, medications may be introduced into the systemic circulation without initially entering the portal circulation where they may be metabolized into a pharmacologically inactive form (first pass effect). For medications that are normally taken orally, transdermal delivery can eliminate factors such as pH changes and food intake that influence gastrointestinal absorption.

In addition, the transdermal administration of medications may allow rapid termination of drug input should side effects occur. Furthermore, there is less discomfort associated with transdermal medication administration, which increases patient compliance over prior medication administration routes. The transdermal route is, therefore, a suitable route for the administration of very potent drugs, drugs with short half lives and low therapeutic indices, drugs which are subject to significant first pass effects, or drugs that cause uncomfortable side effects or are painfully administered.

A number of transdermal drug delivery systems have been developed and are currently in use. These devices, typically in the form of a drug patch, contain the active constituent dispersed or suspended in a reservoir, with its rate of release controlled through passive administration by matrix diffusion or by its passage through a controlling membrane. A drug patch is desirable for patient use because it is inconspicuous, easy to use, and allows the patient to be ambulatory while taking the medication.

The drugs incorporated into these transdermal drug delivery systems include nitroglycerin, which has been used for the treatment and prevention of angina pectoris, scopolamine for the treatment of motion sickness, and nicotine for relieving the symptoms associated with smoking cessation. In addition, cardiac drugs, such as the antihypertensive, clonidine, and steroid hormones such as estradiol have also been successfully delivered through the skin into the body's blood circulation.

Prior art transdermal drug delivery systems that employ passive administration techniques using a drug patch allow only medications having small molecular configurations to be administered. Hence, they are of limited use for medications having large molecular configurations. In addition, the prior art transdermal drug delivery systems are capable of delivering only one medication, which may be unsatisfactory for use with patients suffering from chronic or terminal medical conditions who require several medications.

Moreover, prior art transdermal drug delivery systems do not include monitoring capability. Thus, patients suffering from chronic or terminal medical conditions, or having impaired mental states may still require hospitalization to verify that they are receiving their medications, that the medications are being administered in the correct dosages, and that their vital signs, such as blood pressure, heart rate, and so forth, are remaining in an acceptable range.

SUMMARY OF THE INVENTION

Accordingly, it is an advantage of the present invention that a transdermal medication delivery device is provided.

It is another advantage of the present invention that a transdermal medication delivery device is provided for remote controlled administration of medication to a patient.

It is another advantage of the present invention that a transdermal medication delivery device is provided that delivers more than one medication for absorption through the skin of the patient.

Another advantage of the present invention is that a transdermal medication delivery device is provided that allows the vital signs of a patient to be monitored from a remote location.

Yet another advantage of the present invention is that a transdermal medication delivery device is provided that is comfortable for the patient, biocompatible, mechanically strong, and simple to use, and allows a patient to remain ambulatory while receiving one or more medications.

The above and other advantages of the present invention are carried out in one form by a transdermal medication delivery device for remote controlled administration of a medication for absorption through the skin of a patient. The device includes a chamber containing the medication and a valve having a valve inlet in fluid communication with the chamber and having a valve outlet. A medication delivery component is in fluid communication with the valve outlet and has a surface adapted to be in contact with the skin of the patient when in use. The device further includes a controller for controlling a flow of the medication through the valve and a wireless communication interface in communication with the controller for receiving a medication control message from a remote location. The medication control message instructs the controller to regulate the valve to adjust the flow of the medication from the chamber to the surface of the medication delivery component.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
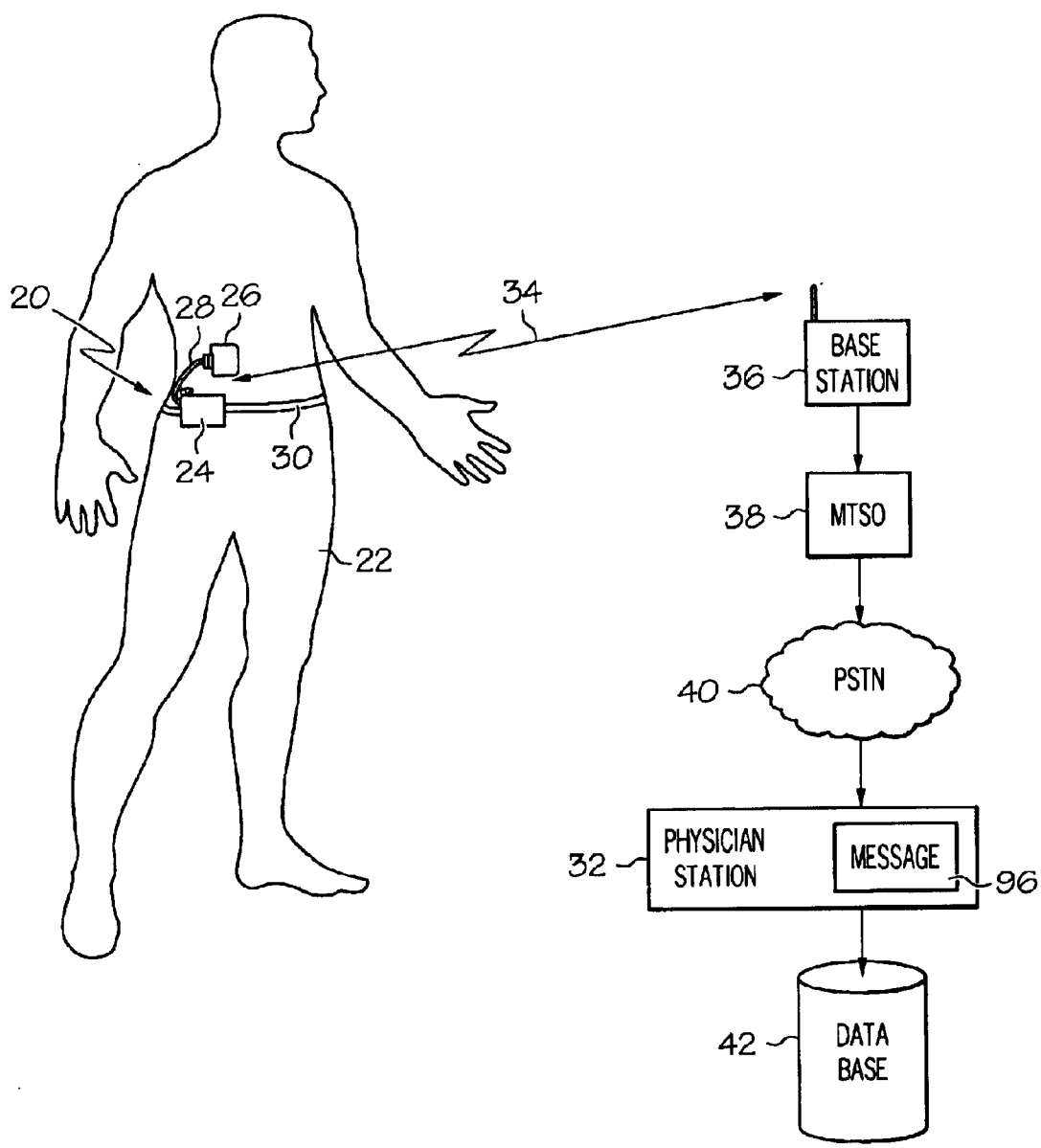
FIG. 1 shows a block diagram of a transdermal medication delivery device worn by a patient in accordance with a preferred embodiment of the present invention.

FIG. 1 shows a block diagram of a transdermal medication delivery device 20 worn by a patient 22 in accordance with a preferred embodiment of the present invention. Generally, device 20 includes a control module 24 and a medication delivery component 26 in fluid communication with module 24 via fluid tubing 28. Control module 24 is retained, for example, through the use of a strap 30 secured about the waist of patient 22, and medication delivery component 26 is adapted to be in contact with the skin of patient 22. Control module 24 contains medications (discussed below) and control circuitry (discussed below) for controlling a flow of the medications to medication delivery component 26 for the eventual absorption through the skin of patient 22.

Transdermal medication delivery device 20 communicates with a remote location, or a physician station 32, via a wireless communication link 34. Wireless communication link 34 is a radio frequency link of a conventional analog or digital cellular network established between device 20 and a cell site, or base station 36 of the network. Base station 36 is linked to a mobile telephone switching office (MTSO) 38 which, in turn, interfaces with the public switched telephone network (PSTN) 40. Physician station 32 is subsequently connected to PSTN 40.

Physician station 32 is located in a hospital, clinic, physician's office, and the like, and communicates with device 20 by periodically dialing a cellular telephone number associated with device 20. A communication path is then established through PSTN 40, MTSO 38, base station 36, and through the establishment of radio communication link 34 using conventional wireline and wireless switching techniques.

Physician station 32 represents a conventional microprocessor-based computer system. Hence, those skilled in the art will recognize that physician station 32 may include features such as memory, a disk drive, keyboard, modem, and so forth (not shown) and will not be discussed in detail herein. Software programs resident in the computer memory of physician station 32 provide the necessary capability to initiate communication with device 20 in order to monitor the operation of device 20, monitor the delivery of the medication from control module 24 to medication delivery component 26, and monitor the vital signs of patient 22 (discussed below). In addition, the monitored parameters associated with patient 22 may be stored in a database 42 in order to maintain a historical record of patient 22. In response to the monitoring operations, medical personnel at physician station 32 can then remotely adjust the amount of medication being administered to patient 22 (discussed below).

Transdermal medication delivery device 20 is particularly suited for use with patients who have chronic or terminal medical conditions and who typically are required to take more than one type of medication on an irregular schedule. By using device 20, patients need not be hospitalized in order to control the administration of the medications and for monitoring purposes. Thus, a patient may remain ambulatory and/or in their own home thereby enhancing the quality of life of the patient and decreasing medical costs associated with the care of the patient over conventional hospitalization practices or in-home, continuous nursing care.

Figure 2:
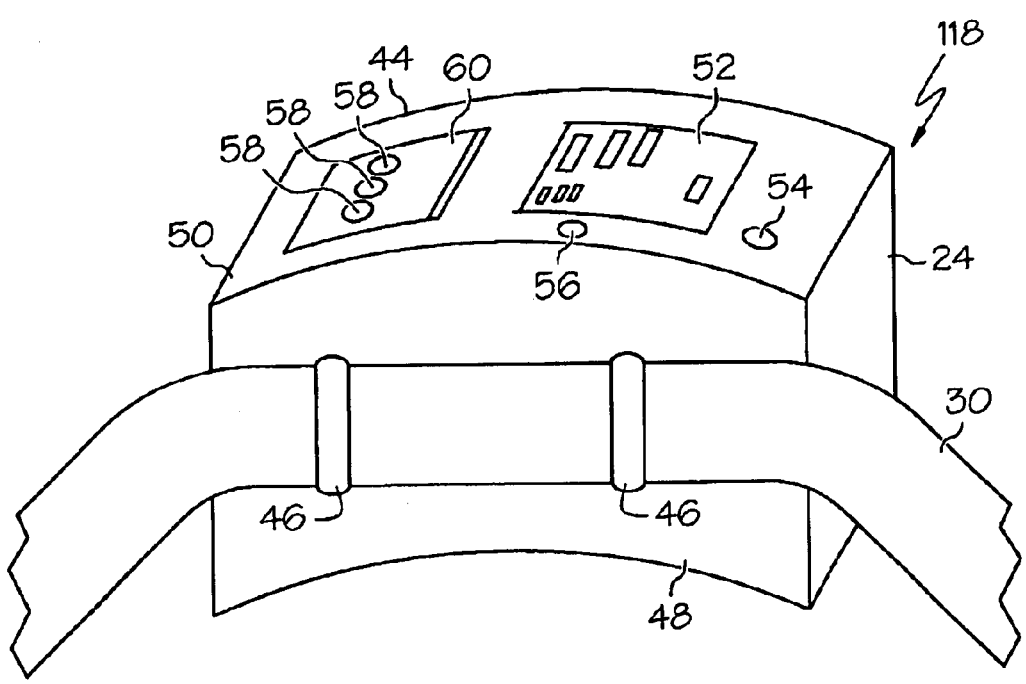
FIG. 2 shows a perspective view of the control module of the transdermal medication delivery device of FIG. 1.

FIG. 2 shows a perspective view of control module 24 of transdermal medication delivery device 20 (FIG. 1). Control module 24 includes a housing 44 and strap 30 directed through two slots 46 on a patient facing side 48 of housing 44. Housing 44 is outwardly convex so that patient facing side 48 curves to fit more comfortably about the waist of patient 22 (FIG. 1). A top side 50 of housing 44 includes a display unit 52, an antenna 54, and a power switch 56. Top side 50 of housing 44 further includes recessed ports 58 covered by a hinged lid 60. Top side 50 of control module 24 may also include other components, such as a system test button, a light emitting diode (LED) indicating that device 20 is powered on, a speaker for providing audible tones, and so forth.

Display unit 52, antenna 54, and power switch 56 are advantageously located on top side 50 for ready presentation to patient 22 (FIG. 1) when worn at the waist. Recessed ports 58 are configured to accommodate vacuum-sealed tubes containing liquid medications (discussed below). Since the medications are in a liquid form, recessed ports 58 are advantageously located on top side 50 to facilitate the flow of the medications from the tubes (discussed below). Device 20 is shown with three of recessed ports 58 for clarity of illustration. However, device 20 may be adapted to include only one recessed port 58 or up to nine recessed ports 58.

Figure 3:
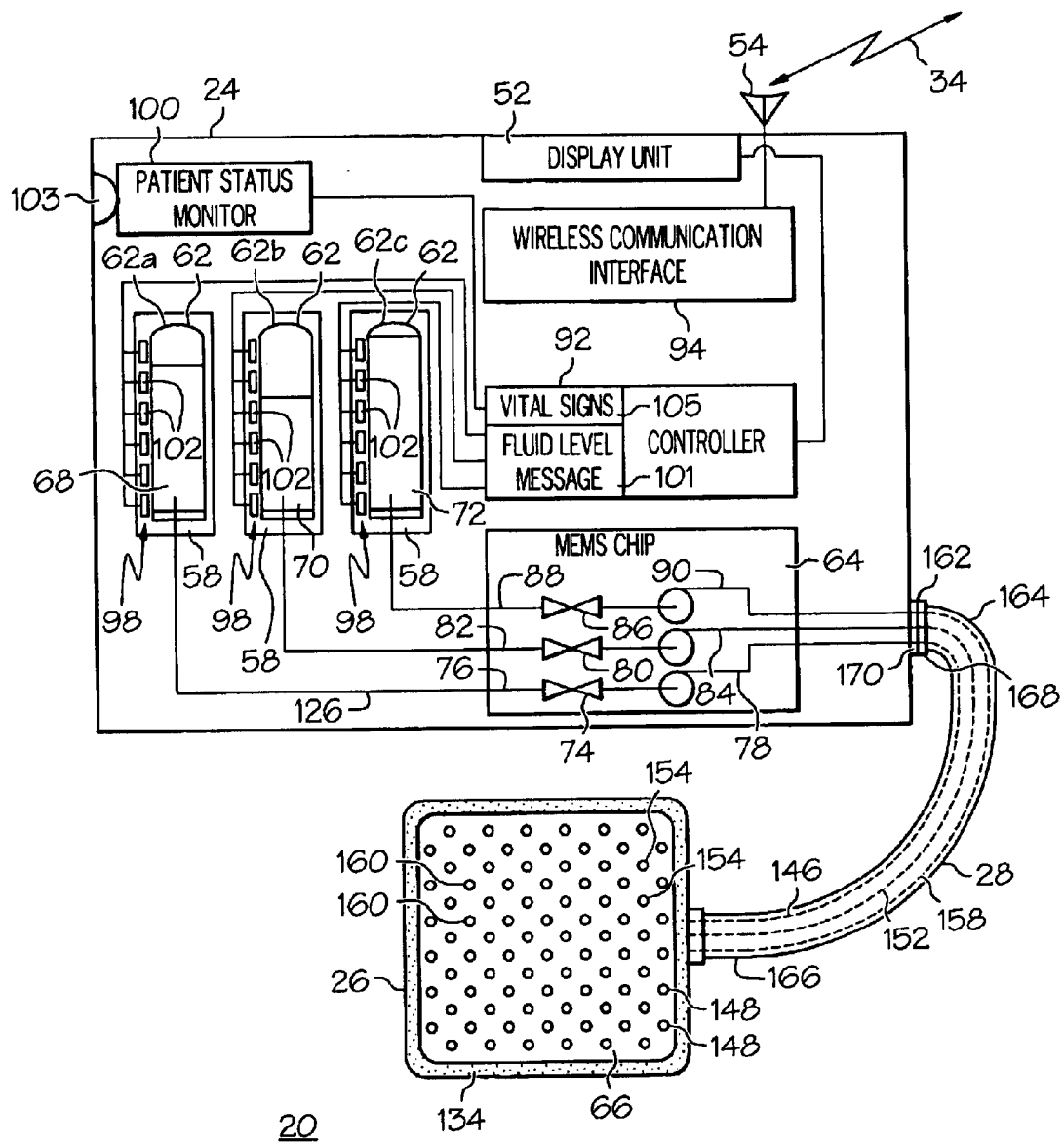
FIG. 3 shows a block diagram of the transdermal medication delivery device.

FIG. 3 shows a block diagram of transdermal medication delivery device 20. Device 20 includes a chamber, or vacuum-sealed tube, 62 containing medication. A micro-electro-mechanical-systems-based (MEMS-based) valve chip 64 is in fluid communication with each of tubes 62. Medication delivery component 26 is in fluid communication with an outlet of MEMS-based chip 64 via fluid tubing 28. Medication delivery component 26 has a surface 66 adapted to be in contact with the skin of patient 22 (FIG. 1) when in use.

In this exemplary embodiment, device 20 includes three tubes 62, each of which is positioned in one of recessed ports 58. A first one of tubes 62, designated 62a, contains a first medication 68. Likewise, a second one of tubes 62, designated 62b, contains a second medication 70, and a third one of tubes 62, designated 62c, contains a third medication 72. The type of medications contained in tubes 62 depend upon a particular medical condition of patient 22. It is anticipated that device 20 may be adapted for use with a number of medications including, but not limited to, dilantin or depakote for the control of seizures; birth control medications; sulfonylureas, biguanides, alpha-glucosidase inhibitors, thiazolidinedione, meglitinide, amino acid D-phenylalanine derivative, and amylin synthetic for the control of diabetes; prescription analgesics, ergot alkloids, triptan drugs, and beta-blockers for pain management; aspirin, digitalis, and nitroglycerin for heart conditions; vitamin complexes; psychotherapeutics for the control of mental conditions; and so forth.

MEMS-based valve chip 64 includes a first valve 74 having a first valve inlet 76 in fluid communication with first tube 62a and having a first valve outlet 78. Likewise, MEMS-based valve chip 64 includes a second valve 80 having a second valve inlet 82 in fluid communication with second tube 62b and having a second valve outlet 84, and a third valve 86 having a third valve inlet 88 in fluid communication with third tube 62c and having a third valve outlet 90.

In a preferred embodiment, valve chip 64 employs micro-electro-mechanical-systems (MEMS) techniques. As known to those skilled in the art, MEMS is the integration of mechanical elements, sensors, actuators, and electronics on a common silicon substrate through the utilization of microfabrication technology. While the electronics are fabricated using integrated circuit process sequences, the micromechanical components are fabricated using compatible "micromachining" processes that selectively etch away parts of the silicon wafer or add new structural layers to form the mechanical and electromechanical devices. Through the use of MEMS technology, mechanical, electromechanical, and electrical element can be combined into small, for example, less than one inch square, components for ready incorporation into portable items, such as device 20.

Each of first, second, and third valves 74, 80, and 86, are silicon fabricated pump driven microvalves formed on a single chip, each having delivery flow rates of 0.01 to 5 milliliters per hour. The microvalve design advantageously utilizes a silicon membrane which deflects to control flow. Hence, there are no sliding or rotating parts that can stick or degrade, thus increasing the durability of MEMS-based valve 64.

Device 20 further includes a controller 92 for controlling flows of first, second, and third medications 68, 70, and 72, respectively, through each of first, second, and third valves 74, 80, and 86, respectively, of said MEMS-based valve chip 64. Controller 92 controls first, second, and third valves 74, 80, and 86 by regulating pump speed and therefore, flow rate/delivery rate of each of first, second, and third medications 68, 70, and 72.

A wireless communication interface 94 is in communication with controller 90. Wireless communication interface 94 includes a dual band transceiver and associated circuitry such as a modem, signal processor, analog-to-digital and digital-to-analog converters, as known to those skilled in the art. Wireless communication interface 94 is in communication with antenna 54 and is capable of accessing both analog and digital networks to ensure quality of signal and extensive coverage. In an alternative embodiment, wireless communication interface 94 may include a tri-band transceiver to accommodate communications over a third network, such as the global system for mobile communications (GSM), which is the standard digital cellular phone service found in Europe, Japan, Australia, and elsewhere.

Wireless communication interface 94 is configured to receive a medication control message 96 (FIG. 1) from physician station 32 (FIG. 1) over communication link 34. Medication control message 96 instructs controller 92 to regulate pump speed of each of first, second, and third valves 74, 80, 86 so as to adjust a flow of first, second, and third medications 68, 70, and 72 from first, second, and third tubes 62a, 62b, 62c, respectively, to surface 66 of medication delivery component 26.

Device 20 further includes fluid level sensors 98 in communication with controller 92 for the remote monitoring of medication administration and dosage information and a patient status monitor 100 in communication with controller 92 for the remote monitoring of patient vital signs.

Fluid level sensors 98 are located in each of recessed ports 58 proximate first, second, and third tubes 62a, 62b, and 62c and provide fluid level signals to controller 92 indicative of a fluid level of first, second, and third medications 68, 70, and 72. In a preferred embodiment, each of fluid level sensors 98 includes a series of capacitive proximity switches 102. Each of medications 68, 70, and 72 acts as the dielectric for switches 102, keeping the contact closed when fluid is present. As the medication level drops, the dielectric effect is lost, and switches 102 open. This alerts controller 92 that the medication level has dropped below the level of any switches 102 that are open. In response, controller 92 generates a fluid level message 101 describing the amount of each of first, second, and third medications 68, 70, and 72, remaining in tubes 62.

Fluid level message 101 may be stored in a memory element (not shown) associated with controller 92 for eventual transmission to physician station 32 (FIG. 1) over communication link 34. In addition, these fluid level signals may be displayed on display unit 52 (discussed below), which is in communication with controller 92. When any of medications 68, 70, and 72 reach the lowest level, i.e., the bottom most one of switches 102 opens, controller 92 may also send an audible alert tone via a speaker (not shown) on housing 44 (FIG. 2) of control module 24 to audibly alert patient 22 (FIG. 1) that one of tubes 62a, 62b, and 62c is empty and requires replacement.

Figure 5:
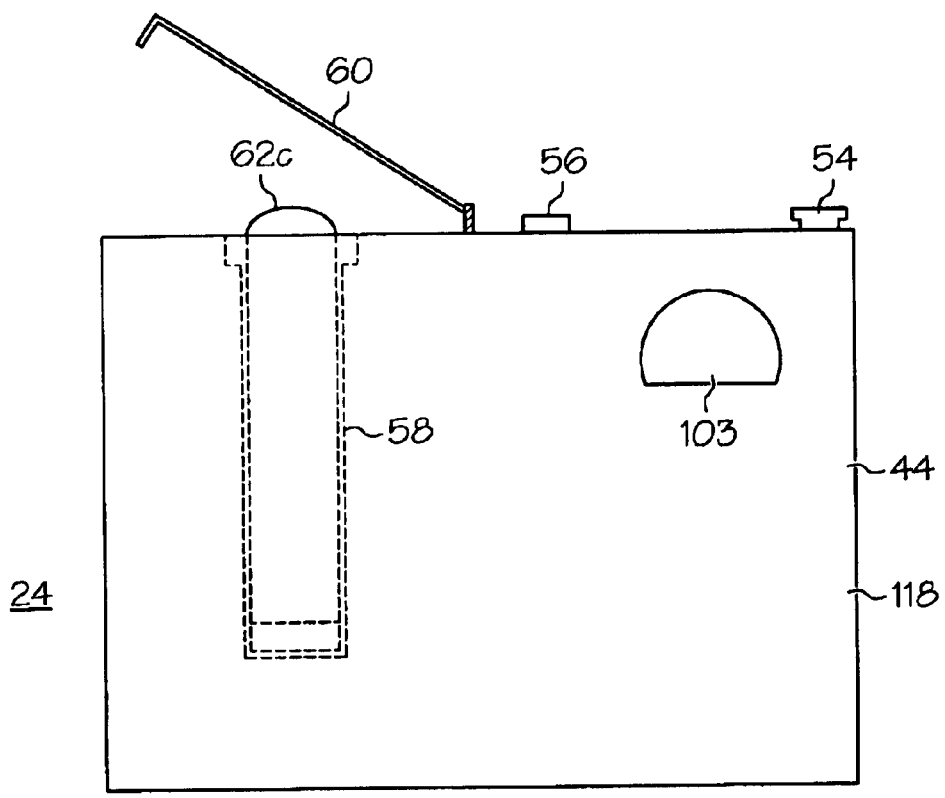
FIG. 5 shows a front view of the control module.

Patient status monitor 100, integral to housing 44 (FIG. 2) of control module 24, monitors vital signs of patient 22 (FIG. 1). Vital signs include at least one of a heart rate, blood pressure, temperature, and blood oxygen level. Patent status monitor 100 includes a finger insertion port 103 extending into housing 44 (as best seen in FIG. 5). The vital signs of patient 22 (FIG. 1) are periodically monitored from one of the fingers of patient 22.

Patient status monitor 100 is adapted from commercially available technology to fit within control module 24. Commercially available technology includes, for example, finger-activated opto-electric sensors that measure the change in light intensity as blood flows through a blood vessel of the finger. This change in light intensity is used to detect heart rate. Finger worn pulse oximeters are photo electric devices that employ infrared sensors to calculate blood oxygen level, i.e., oxygen saturation, in order to monitor pulmonary function. Other technologies include miniature blood pressure/heart rate units that include an auto-inflating finger cuff for detecting blood pressure and heart rate from the finger. Still other technologies include finger worn temperature sensors for detecting the skin temperature of the finger.

Vital signs 105, such as blood pressure, heart rate, temperature and/or blood oxygen level, are communicated to controller 92 and may be stored in a memory element associated with controller 92 for eventual transmission to physician station 32 (FIG. 1) over communication link 34. In addition, vital signs 105 may be displayed on display unit 52 (discussed below), which is in communication with controller 92.

Figure 4:
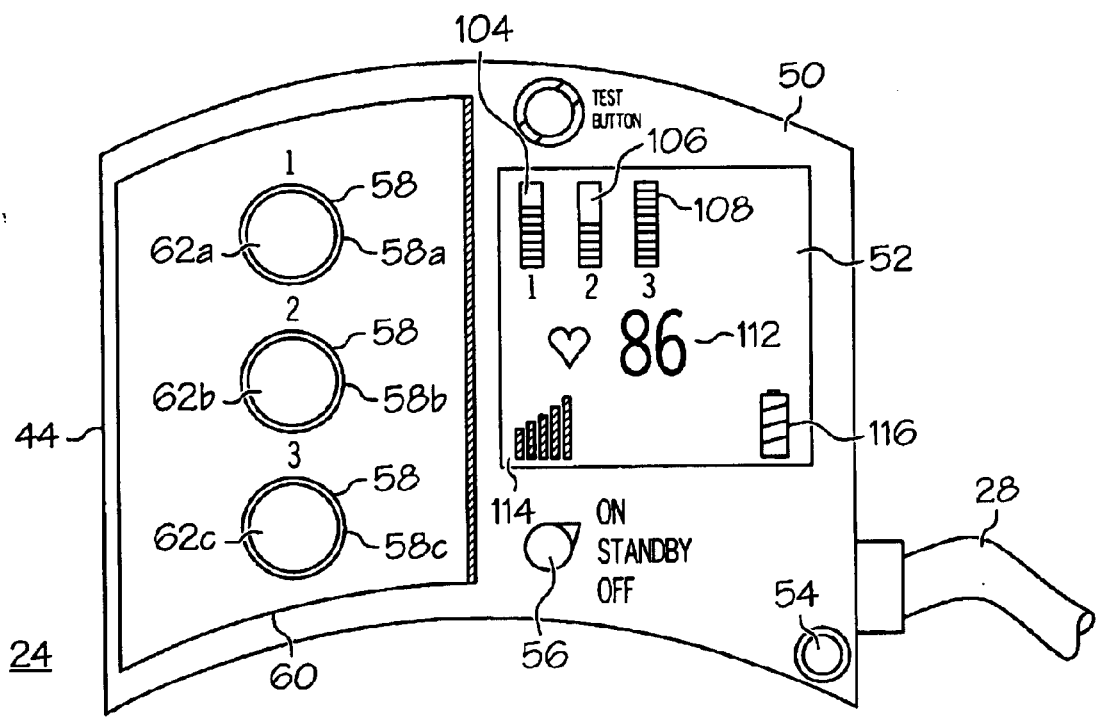
FIG. 4 shows a top view of the control module.

FIG. 4 shows a top view of control module 24 of transdermal medication delivery device 20. In particular, top side 50 including display unit 52, antenna 54, power switch 56, and recessed ports 58 below hinged lid 60 are shown. First tube 62a is positioned in a first one of recessed ports 58, designated 58a. Likewise, second tube 62b is positioned in a second one of recessed ports 58, designated 58b, and third tube 62c is positioned in a third one of recessed ports.

Display unit is desirably a low power draw liquid crystal display (LCD) for displaying medication levels of fluid level message 101, patient vital signs 105, signal strength, and battery strength. By way of example, display unit 52, controlled by controller 92 (FIG. 3), displays a first fluid level signal 104 corresponding to a quantity of first medication 68 (FIG. 3) remaining in first tube 62a, as sensed by its corresponding fluid level sensor 98 (FIG. 3). Similarly, display unit 52 displays a second fluid level signal 106 corresponding to a quantity of second medication 70 (FIG. 3) remaining in second tube 62b, as sensed by its corresponding fluid level sensor 98 (FIG. 3). Likewise, display unit 52 displays a third fluid level signal 108 corresponding to a quantity of third medication 72 (FIG. 3) remaining in third tube 62c, as sensed by its corresponding fluid level sensor 98 (FIG. 3).

Display unit 52 further includes a heart rate reading 112 for patient 22 (FIG. 1), a signal strength display 114 and a battery level indicator 116. Signal strength display 114 displays the strength of control signaling between the wireless network, i.e., base station 36 and antenna 54. Battery level indicator 116 shows the amount of charge remaining on the battery (not shown) within control module 24. Each of these parameters, viewable on display unit 52 are also periodically communicated from controller 92 (FIG. 3) using wireless communication interface 94 to physician station 32 (FIG. 1), as discussed previously.

FIG. 5 shows a front view of control module 24 of transdermal medication delivery device 20. Finger insertion port 103 is located on an outward facing side 118 (see also FIG. 2) of control module 24 for ready access by patient 22. FIG. 5 also shows hinged lid 60 in an open position. Tubes 62, third tube 62c being the only one visible, protrude slightly above top side 50 of control module 24 so that tubes 62 may be inserted into and lifted out of recessed port 58, shown in ghost form.

In a preferred embodiment, hinged lid 60 is a spring-hinge push-release cover that allows access to recessed ports 58. Hinged lid 60 may optionally include a locking mechanism so that hinged lid 60 may be locked closed when device 20 is configured to deliver narcotics.

Figure 6:
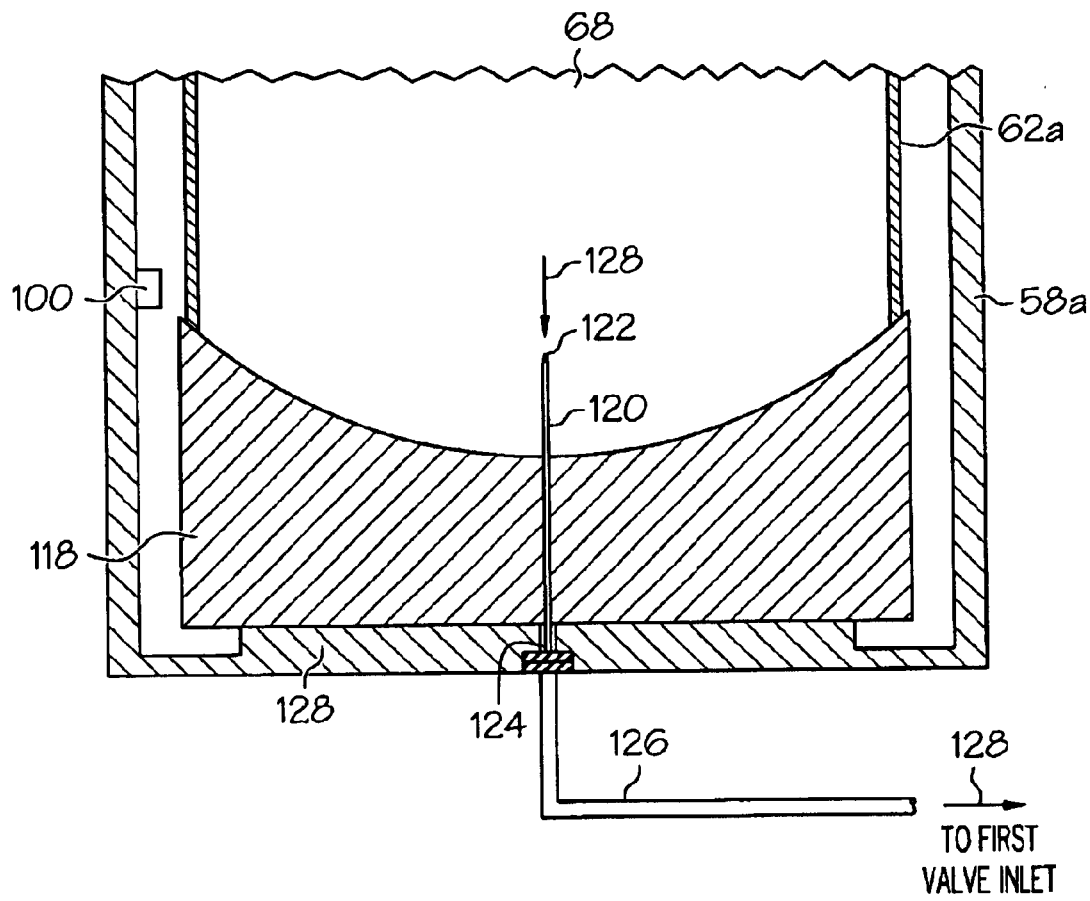
FIG. 6 shows a sectional view of a bottom portion of one of the recessed ports in a housing of control module.

FIG. 6 shows a sectional view of a bottom portion of one of recessed ports 58 in housing 44 (FIG. 2) of control module 24. FIG. 6 further shows one of tubes 62, containing medication, positioned in recesses port 58. For clarity of illustration, the one of recessed ports 58 is first recessed port 58a in which first tube 62a, containing medication 68, is positioned. Although the following description is discussed in terms of first recessed port 58a, first tube 62a, and first medication 68, the following teaching applies equally to all of ports 58 and tubes 62.

As discussed briefly above, first valve inlet 76 (FIG. 2) is in fluid communication with first tube 62a. More specifically, first tube 62a is a vacuum-sealed tube having a self-sealing rubber cap 118. Transdermal medication delivery device 20 further includes a hollow needle 120 having a first end 122 and a second end 124. First end 122 projects into recessed port 58a to pierce self-sealing rubber cap 118 and second end 124 is coupled to a conduit 126 interposed between second end 124 and first valve inlet 76 (see FIG. 3). Thus, first medication 68 is drawn out of first tube 62a, through hollow needle 120 and into conduit 126 to first valve inlet 76, as indicated by arrows 128.

In a preferred embodiment, tubes 62 are conventional glass, vacuum-sealed tubes having rubber caps and configured to contain approximately six cubic centimeters (cc) of medication such as, first medication 68. Hollow needle 120 is a conventional ten-gauge stainless steel needle. Tube 62a is positioned in first recessed port 58a until first end 122 of needle 120 pierces self-sealing rubber cap 118 and cap 118 abuts a pedestal 128 at the bottom of recessed port 58a. Thus, tubes 62 are readily positioned in recessed ports 58 and readily replaced when empty.

Figure 7:
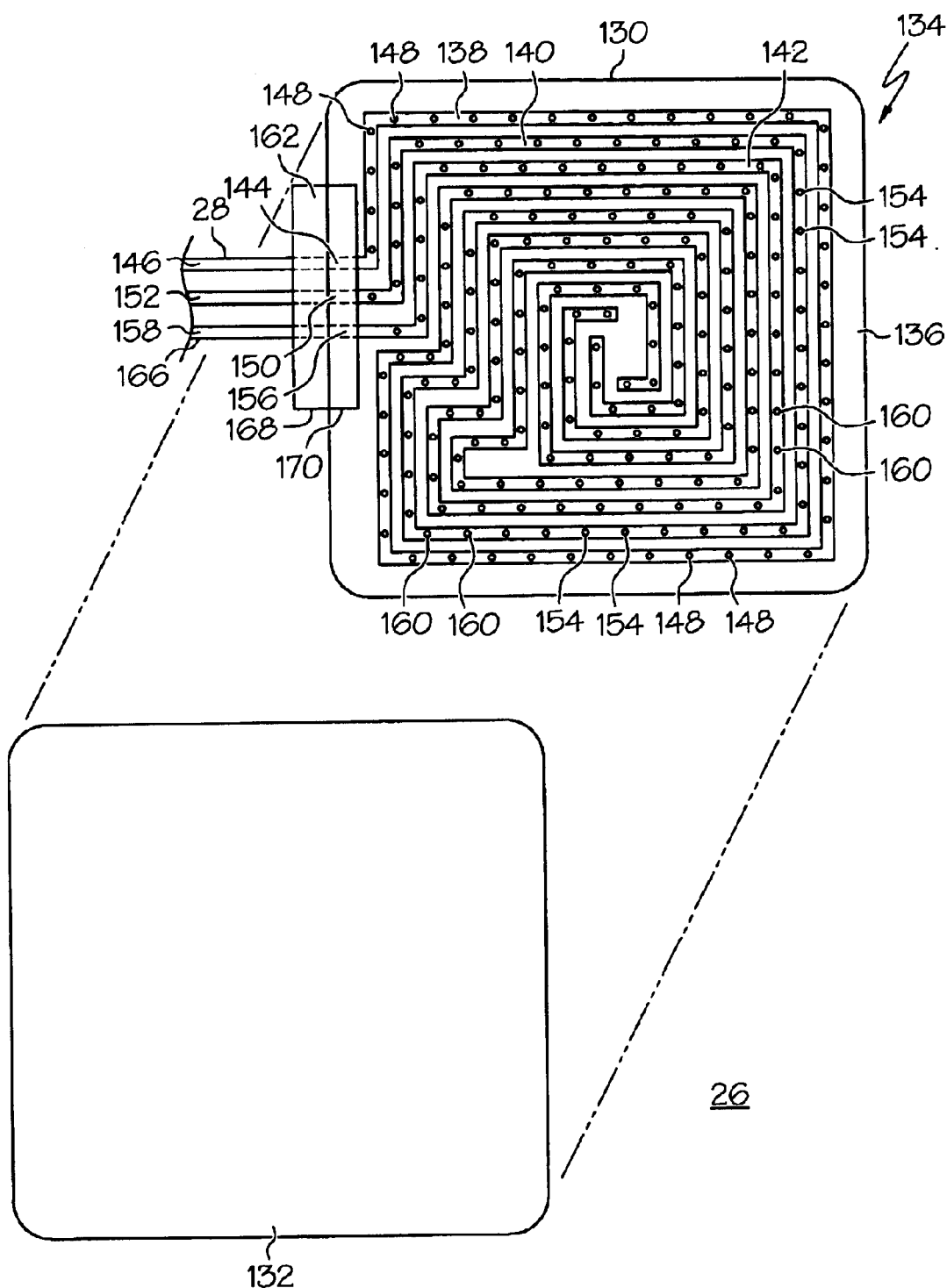
FIG. 7 shows an exploded view of a medication delivery component of the transdermal medication delivery device.

FIG. 7 shows an exploded view of medication delivery component 26 of transdermal medication delivery device 20 (FIG. 3). Medication delivery component 26 includes a base layer 130 and a top layer 132. Medication delivery component 26 is a patch system having an adhesive portion 134 (FIG. 3) along an outer perimeter of surface 66 (FIG. 3) so that medication delivery component 26 may be adhered to the skin of patient 22.

Base layer 130 includes surface 66 (see also FIG. 3), and an inner side 136 opposing surface 66. Base layer further includes first, second, and third channels 138, 140, and 142, respectively, integral to inner side 136. In a preferred embodiment, base layer 130 is a milled Teflon® base having a thickness of approximately 0.05 inches. First, second, and third channels 138, 140, and 142 project from base layer 130 at a height of approximately 0.025 inches. Top layer 132 covers and encloses each of first, second, and third channels 138, 140, and 142 and is coupled to base layer 130. In particular, top layer 132 is a Teflon® layer polyfused to base layer 130, thus forming a thickness of medication delivery component 26 of less than 0.1 inch.

First channel 138 includes a first channel inlet 144 in fluid communication with first valve outlet 78 (FIG. 3). More specifically, a first duct portion 146 (also represented by a dashed line in FIG. 3) of fluid tubing 28 is interposed between first valve outlet 78 and first channel inlet 144. First channel 138 further includes first channel outlets 148 (see also FIG. 3) extending through surface 66 of base layer 130. In a preferred embodiment, first channel outlets 148 are approximately 0.001 inch in diameter and are spaced-apart at approximately 0.25 inch intervals.

Second and third channels 140 and 142 are configured similarly. That is, second channel 140 includes a second channel inlet 150 in fluid communication with second valve outlet 84 via a second duct portion 152 (also represented by a dashed line in FIG. 3) of fluid tubing 28 interposed between second valve outlet 84 and second channel inlet 150. Second channel 140 also includes second channel outlets 154 (see also FIG. 3) extending through surface 66 of base layer 130. Likewise, third channel 142 includes a third channel inlet 156 in fluid communication with third valve outlet 90 via a third duct portion 158 (also represented by a dashed line in FIG. 3) of fluid tubing 28 interposed between third valve outlet 90 and third channel inlet 156. Third channel 142 also includes third channel outlets 160 (see also FIG. 3) extending through surface 66 of base layer 130.

In a preferred embodiment, medication delivery component 26 is an approximately two inch by two inch patch configured for the passive administration of first, second, and third medications 68, 70, and 72 from surface 66 for absorption through the skin of patient 22. That is, the rate of release of first, second, and third medications 68, 70, and 72 is controlled by their passage through each of first, second, and third channel outlets 146, 152, and 158, respectively.

First, second, and third channels 138, 140, and 142, respectively, are milled into base layer 130 so that first, second, and third channel outlets 146, 152, and 158 are arranged in a generally inwardly spiraling pattern in base layer 130. This arrangement, maximizes the number of first, second, and third channel outlets 146, 152, and 158 over surface 66 and distributes outlets 146, 152, and 158 across surface 66 to desirably maximize an absorption rate of first, second, and third medications 68, 70, and 72 (FIG. 3) into the skin of patient 22 (FIG. 1).

Referring momentarily to FIG. 3, fluid tubing 28 may be integral with medicine delivery component 26. As such, a quick-disconnect coupling 162 interconnects first, second, and third valve outlets 78, 84, and 90 with first, second, and third duct portions 146, 152, and 158 of fluid tubing 28, and consequently with medication delivery component 26. More specifically, coupling 162 is utilized to interconnect a first end 164 of fluid tubing 28 to valve outlets 78, 84, and 90. In addition, as shown in FIG. 7, device 20 may also include a second quick-disconnect coupling 162 on a second end 166 of fluid tubing 28 so that fluid tubing is a separate unit from each of control module 24 and medication delivery component 26.

In a preferred embodiment coupling 162 is a self-sealing, quick-disconnect coupling such as those manufactured by CPS Colder Products Company, St. Paul, Minn. In operation, when an insert portion 168 of coupling 162 at first end 164 of fluid tubing 28 is snapped into a body portion 170 of coupling 162 mounted on housing 44 of control module 24, first, second, and third valve outlets 78, 84, and 90 are in fluid communication with medication delivery component 26. In addition, when insert portion 168 of coupling 162 is disconnected from body portion 170, each of insert and body portions 168 and 170, respectively, are self-sealing to prevent leakage of first, second, and third medications 68, 70, and 72 from device 20.

Figure 8:
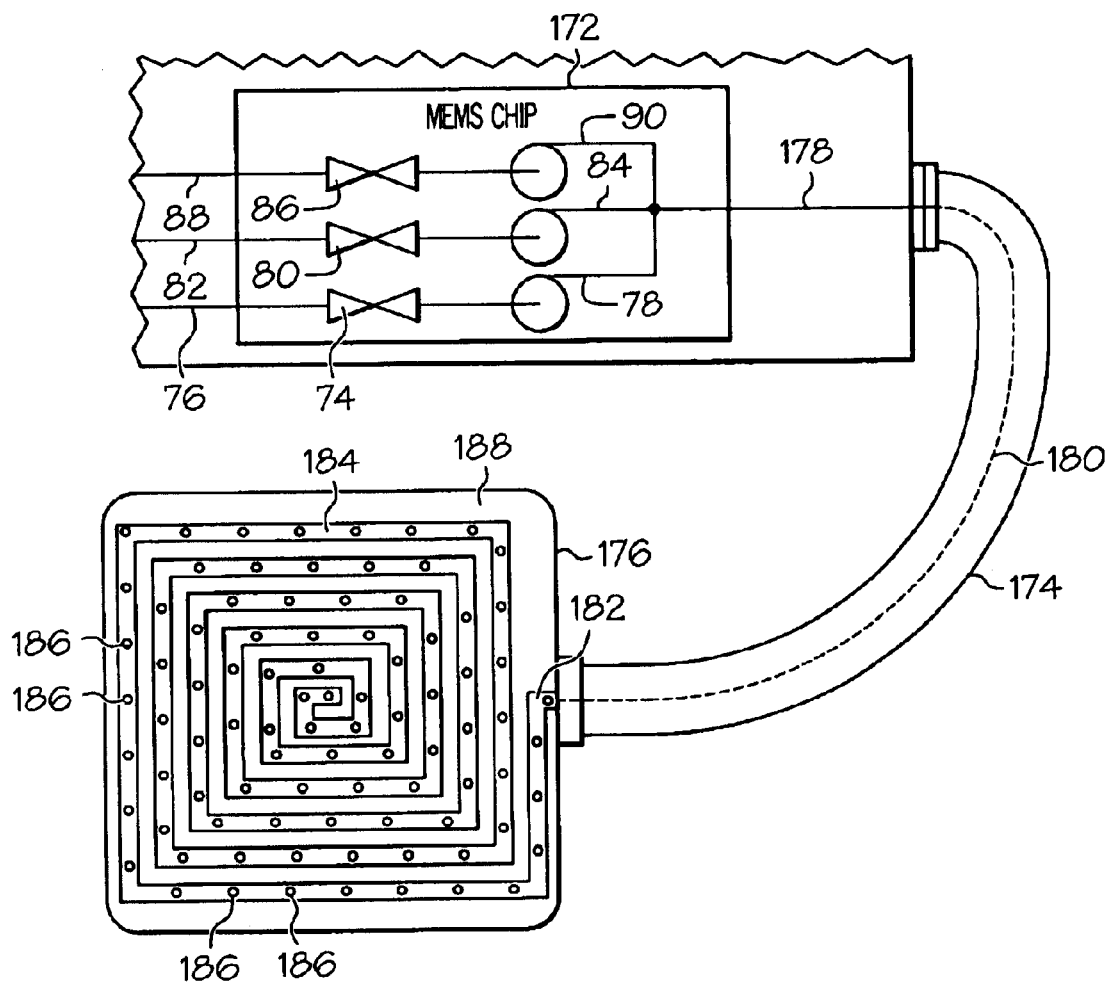
FIG. 8 shows a block diagram of a MEMS-based valve chip used in the control module of the transdermal medication delivery device in accordance with an alternative embodiment of the present invention.

FIG. 8 shows a block diagram of a MEMS-based valve chip 172 used in control module 24 (FIG. 3) of transdermal medication delivery device 20 (FIG. 3) in accordance with an alternative embodiment of the present invention. FIG. 8 further shows fluid tubing 174, and a medication delivery component 176 compatible with the design of MEMS-based valve chip 172. MEMS-based valve chip 172, fluid tubing 174, and medication delivery component 176 may be employed in place of valve chip 64, fluid tubing 28, and medication delivery component 26 (FIG. 3).

In particular, valve chip 64, fluid tubing 28, and medication delivery component 26 provide multiple streams of first, second, and third medications 68, 70, and 72 (FIG. 3) at surface 66 (FIG. 3) of medication delivery component 26. Alternatively, MEMS-based valve chip 172 provides a combined stream of first, second, and third medications 68, 70, and 72.

Like valve chip 64, MEMS-based valve chip 172 includes first valve 74 having first valve inlet 76 and first valve outlet 78. Likewise, MEMS-based valve chip 172 includes second valve 80 having second valve inlet 82 and second valve outlet 84, and third valve 86 having third valve inlet 88 and third valve outlet 90. However, downstream tubing 178 interconnects with each of first, second, and third valve outlets 78, 84, and 90. Accordingly, first, second, and third medications 68, 70, and 72, flowing through first, second, and third valves 74, 80, and 86 are combined in downstream tubing 178.

Fluid tubing 164 includes a single duct portion 180 for conveying the combined, first, second, and third medications 68, 70, and 72 to a channel inlet 182 of a single channel 184 of medication delivery component 176. Medication delivery component 176 is fabricated similarly to medication delivery component 26 (FIG. 7) except that component 176 includes only one channel 184, as opposed to first, second, and third channels 138, 140, and 142 (FIG. 7) of component 26. Channel 184 further includes channel outlets 186 at a skin contacting surface 188 of medication delivery component 176 for delivery of a combined flow of first, second, and third medications 68, 70, and 72 to the skin of patient 22 (FIG. 1).

The combined flow of medications 68, 70, and 72, simplifies the design and fabrication of fluid tubing 174 and medication delivery component 176 over fluid tubing 28 (FIG. 3) and medication delivery component 26 (FIG. 7). In addition, the absorption of some medications may be improved by combining them in downstream tubing 178 with a penetration enhancer or a combination of penetration enhancers. That is, many of the drugs that are otherwise suitable for transdermal delivery do not achieve sufficiently high blood levels for pharmacological activity when administered transdermally so that it is sometimes necessary to enhance this delivery. This can be achieved by chemical means namely by combining the medication with penetration enhancers, also known as absorption promoters. Penetration enhancers include, for example, aprotic solvents, such as dimethylsulfoxide (DMSO), Azone® and some surfactants. Accordingly, one or more of tubes 62 (FIG. 3)

may include penetration enhancers, while another of tubes 62 includes the medication, so that following their flow through valves 74, 80, and 86 they will combine in downstream tubing 178.

With reference back to FIG. 3, in operation transdermal medication delivery device 20 is first activated at a physician's clinic or hospital. First, second, and third medications 68, 70, and 72 are positioned in recessed ports 58, medication delivery component 26 (or alternatively, 176) is attached to the skin of patient 22 (FIG. 1), and power switch 56 (FIG. 4) is activated. Device 20 powers up in a standby mode so that each of first, second, and third valves 76, 82, and 88 are closed. Medical personnel can then control device 20 via wireless communication link 34 using, for example, a low power, close proximity wireless base station in communication with physician station 32 (FIG. 1).

Medical personnel can set initial doses for the administration of medications 68, 70, and 72. These initial doses are converted at physician station 32 (FIG. 1) into medication control message 96 and communicated to device 20. Patient 22 is then free to leave the vicinity of the medical personal. Medical personnel can refer to physician station 32 for periodic status reports that include fluid level message 101 to determine the quantity of medication administered to patient 22 and vital signs 105 of patient 22. In response to fluid level message 101 and vital signs 105, medical personnel may then transmit an updated medication control message to device 20 via wireline and wireless communication networks to adjust the flows of each of first, second, and third medications 68, 70, and 72.

In summary, the present invention teaches of a transdermal medication delivery device. The medication delivery component adhered to the patient's skin is small and low profile so as to be comfortable to the patient, and the control module is miniaturized and made durable through the use of miniaturized components, such as the MEMS-based valve chip. This small size precludes the need for hospitalization so that a patient may remain ambulatory and/or in their own home. In addition, since the device administers medications in accordance with control messages provided by medical person, the patient or caregiver need not remember complicated medication schedules. Thus, the device is simple to use. The transdermal medication administration route is less invasive and less likely to cause side effects than prior injection, oral, and nasal routes, thus increasing patient compliance. The device includes a wireless communication interface that allows the administration of the medication to be adjusted from a remote location over a wireless communication link of a wireless network. In addition, vital signs and fluid levels of medication in the device can be monitored from the remote location through the radio communication link.

Although the preferred embodiments of the invention have been illustrated and described in detail, it will be readily apparent to those skilled in the art that various modifications may be made therein without departing from the spirit of the invention or from the scope of the appended claims. For example, the transdermal medication delivery device may include more or less than three recessed ports for administering more or less than three medications.

What is claimed is:

1. A transdermal medication delivery device for remote controlled administration of a medication for absorption through the skin of a patient, said device comprising:

a chamber containing said medication, said chamber being a tube having a self-sealing cap;

a valve having a valve inlet in fluid communication with said chamber and having a valve outlet;

a housing having a recessed port in which said tube of said chamber is positioned, and a hollow needle having a first end and a second end, said first end projecting into said recessed port to pierce said self-sealing cap, and said second end being in fluid communication with said valve inlet;

a medication delivery component in fluid communication with said valve outlet and having a surface adapted to be in contact with said skin of said patient when in use;

a controller for controlling a flow of said medication through said valve; and a wireless communication interface in communication with said controller for receiving a medication control message from a remote location, said medication control message instructing said controller to regulate said valve to adjust said flow of said medication from said chamber to said surface of said medication delivery component.

2. A device as claimed in claim 1 wherein said housing further includes a hinged lid covering said recessed port.

3. A transdermal medication delivery device for remote controlled administration of a medication for absorption through the skin of a patient, said device comprising:

a chamber containing said medication;

a valve having a valve inlet in fluid communication with said chamber and having a valve outlet, said valve being a micro-electromechanical systems-based (MEMS-based) microvalve architecture;

a medication delivery component in fluid communication with said valve outlet and having a surface adapted to be in contact with said skin of said patient when in use;

a controller for controlling a flow of said medication through said valve; and a wireless communication interface in communication with said controller for receiving a medication control message from a remote location, said medication control message instructing said controller to regulate said valve to adjust said flow of said medication from said chamber to said surface of said medication delivery component.

4. A transdermal medication delivery device for remote controlled administration of a medication for absorption through the skin of a patient, said device comprising:

a chamber containing said medication;

a valve having a valve inlet in fluid communication with said chamber and having a valve outlet;

a medication delivery component in fluid communication with said valve outlet and having a surface adapted to be in contact with said skin of said patient when in use, said medication delivery component including:

a base layer having said surface and having an inner side;

a channel integral to said inner side of said base layer, said channel having a channel inlet in fluid communication with said valve outlet and having channel outlets extending through said surface of said base layer; and a top layer coupled to said inner side of said base layer and enclosing said channel;

a controller for controlling a flow of said medication through said valve; and a wireless communication interface in communication with said controller for receiving a medication control message from a remote location, said medication control message instructing said controller to regulate said valve to adjust said flow of said medication from said chamber to said surface of said medication delivery component.

5. A device as claimed in claim 4 wherein said channel outlets are arranged in a generally inwardly spiraling pattern at said surface.

6. A transdermal medication delivery device for remote controlled administration of a medication for absorption through the skin of a patient, said device comprising:
   a chamber containing said medication;
   a valve having a valve inlet in fluid communication with said chamber and having a valve outlet;
   a medication delivery component in fluid communication with said valve outlet and having a surface adapted to be in contact with said skin of said patient when in use, said medication delivery component including an adhesive portion for adhered connection of said medication delivery component to said skin of said human;
   a controller for controlling a flow of said medication through said valve; and
   a wireless communication interface in communication with said controller for receiving a medication control message from a remote location, said medication control message instructing said controller to regulate said valve to adjust said flow of said medication from said chamber to said surface of said medication delivery component.

7. A transdermal medication delivery device for remote controlled administration of a medication for absorption through the skin of a patient, said device comprising:
   a chamber containing said medication;
   a valve having a valve inlet in fluid communication with said chamber and having a valve outlet;
   a medication delivery component in fluid communication with said valve outlet and having a surface adapted to be in contact with said skin of said patient when in use;
   a quick-disconnect coupling interconnecting said valve outlet with said medication delivery component;
   a duct portion interconnected between said valve outlet and said medication delivery component, said quick-disconnect coupling interconnecting a first end of said duct portion with said valve outlet;
   a second quick-disconnect coupling interconnecting a second end of said duct portion to an inlet of said medication delivery component;
   a controller for controlling a flow of said medication through said valve; and
   a wireless communication interface in communication with said controller for receiving a medication control message from a remote location, said medication control message instructing said controller to regulate said valve to adjust said flow of said medication from said chamber to said surface of said medication delivery component.

8. A transdermal medication delivery device for remote controlled administration of a first medication and a second medication for absorption through the skin of a patient, said device comprising:
   a first chamber containing said first medication;
   a first valve having a valve inlet in fluid communication with said first chamber and having a valve outlet;
   a medication delivery component in fluid communication with said valve outlet and having a surface adapted to be in contact with said skin of said patient when in use;
   a second chamber containing a second medication;
   a second valve having a second valve inlet in fluid communication with said second chamber and having a second valve outlet in fluid communication with said medication delivery component for delivering a flow of said second medication to said surface of said medication delivery component;
   a controller for controlling a flow of said first medication through said first valve; and
   a wireless communication interface in communication with said controller for receiving a medication control message from a remote location, said medication control message instructing said controller to regulate said first valve to adjust said flow of said first medication from said first chamber to said surface of said medication delivery component.

9. A device as claimed in claim 8 wherein said control message includes instructions for regulating each of said first and second valves.

10. A device as claimed in claim 8 wherein said medication delivery component comprises:
    a first channel having a first channel inlet in fluid communication with said valve outlet of said first valve and having first channel outlets at said surface of said medication delivery component; and
    a second channel having a second channel inlet in fluid communication with said second valve outlet and having second channel outlets at said surface of said medication delivery component.

11. A device as claimed in claim 8 wherein said medication delivery component includes a channel having a channel inlet in communication with said valve outlet of said first valve and in communication with said second valve outlet, said channel further including channel outlets at said surface of said medication delivery component.

12. A transdermal medication delivery device for remote controlled administration of a medication for absorption through the skin of a patient, said device comprising:
    a chamber containing said medication;
    a valve having a valve inlet in fluid communication with said chamber and having a valve outlet;
    a medication delivery component in fluid communication with said valve outlet and having a surface adapted to be in contact with said skin of said patient when in use;
    a controller for controlling a flow of said medication through said valve;
    a wireless communication interface in communication with said controller for receiving a medication control message from a remote location, said medication control message instructing said controller to regulate said valve to adjust said flow of said medication from said chamber to said surface of said medication delivery component; and
    a fluid level sensor proximate said chamber for providing a fluid level signal to said controller indicative of a fluid level of said medication in said chamber.

13. A device as claimed in claim 12 wherein said controller generates a fluid level message in response to said fluid level signal, and said wireless communication interface communicates said fluid level message to said remote location.

14. A device as claimed in claim 12 further comprising a display unit controlled by said controller for displaying said fluid level signal.

15. A transdermal medication delivery device for remote controlled administration of medications for absorption through the skin of a patient, said device comprising:

a first chamber containing a first one of said medications and having a first self-sealing cap;

a second chamber containing a second one of said medications and having a second self-sealing cap;

a housing including a first recessed port in which said first chamber is positioned, a first hollow needle having a first end and a second end, said first end projecting into said first recessed port to pierce said self-sealing cap of said first chamber, and said housing further including a second recessed port in which said second chamber is positioned, a second hollow needle having a third end and a fourth end, said third end projecting into said second recessed port to pierce said self-sealing cap of said second chamber;

a first valve having a first valve inlet and a first valve outlet, said first valve inlet being in fluid communication with said second end of said first hollow needle;

a second valve having a second valve inlet and a second valve outlet, said second valve inlet being in fluid communication with said fourth end of said second hollow needle;

a medication delivery component in fluid communication with each of said first and second valve outlets and having a surface adapted to be in contact with said skin of said patient when in use;

a controller for controlling a flow of said first and second medications through each of said first and second valves; and a wireless communication interface in communication with said controller for receiving a medication control message from a remote location, said medication control message instructing said controller to regulate said first and second valves to adjust said flow of said first medication from said first chamber to said surface of said medication delivery component and to adjust said flow of said second medication from said second tube to said surface of said medication delivery component.

16. A device as claimed in claim 15 wherein said medication delivery component comprises:

a first channel having a first channel inlet in fluid communication with said first valve outlet and having first channel outlets at said surface of said medication delivery component; and a second channel having a second channel inlet in fluid communication with said second valve outlet and having second channel outlets at said surface of said medication delivery component.

17. A device as claimed in claim 15 wherein said medication delivery component includes a channel having a channel inlet in communication with each of said first and second valve outlets, said channel further including channel outlets at said surface of said medication delivery component.

18. A transdermal medication delivery device for remote controlled administration of a medication for absorption through the skin of a patient, said device comprising:

a chamber containing said medication;

a valve having a valve inlet and a valve outlet, said valve inlet being in fluid communication with said chamber;

a medication delivery component in fluid communication with said valve outlet and having a surface adapted to be in contact with said skin of said patient when in use;

a controller for controlling a flow of said medication through said valve;

a fluid level sensor proximate said chamber for providing a fluid level signal to said controller indicative of a fluid level of said medication in said chamber, said controller generating a fluid level message corresponding to said fluid level signal;

a patient status monitor integral to a housing of said device and in communication with said controller for monitoring vital signs of said patient; and a wireless communication interface in communication with said controller for communicating said fluid level message and said vital signs to said remote location, and for receiving a medication control message from a remote location, said medication control message instructing said controller to regulate said valve to adjust said flow of said medication from said chamber to said surface of said medication delivery component.

* * * * *